(12) United States Patent
Kim et al.

(10) Patent No.: US 11,096,877 B2
(45) Date of Patent: Aug. 24, 2021

(54) PERFUME COMPOSITION CAPABLE OF MASKING ODOR OF FORMULATION CONTAINING AMINE

(71) Applicant: LG HOUSEHOLD & HEALTH CARE LTD., Seoul (KR)

(72) Inventors: Hoo-Deok Kim, Daejeon (KR); Ji-Min Lee, Daejeon (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 16/089,749

(22) PCT Filed: Mar. 29, 2016

(86) PCT No.: PCT/KR2016/003207
§ 371 (c)(1),
(2) Date: Sep. 28, 2018

(87) PCT Pub. No.: WO2017/171110
PCT Pub. Date: Oct. 5, 2017

(65) Prior Publication Data
US 2019/0274938 A1    Sep. 12, 2019

(51) Int. Cl.
| | |
|---|---|
| A61K 8/41 | (2006.01) |
| A61K 8/33 | (2006.01) |
| A61Q 5/10 | (2006.01) |
| A61Q 13/00 | (2006.01) |
| A61Q 5/00 | (2006.01) |
| A61K 8/30 | (2006.01) |
| C11D 3/00 | (2006.01) |
| C11D 3/50 | (2006.01) |

(52) U.S. Cl.
CPC ............ *A61K 8/41* (2013.01); *A61K 8/30* (2013.01); *A61K 8/33* (2013.01); *A61K 8/416* (2013.01); *A61Q 5/00* (2013.01); *A61Q 5/10* (2013.01); *A61Q 13/00* (2013.01); *C11D 3/0068* (2013.01); *C11D 3/50* (2013.01)

(58) Field of Classification Search
CPC ............ A61K 8/41; A61Q 5/10; A61Q 13/00
See application file for complete search history.

(56) References Cited

U.S. PATENT DOCUMENTS

| | | | | |
|---|---|---|---|---|
| 4,466,806 A | * | 8/1984 | Bugaut | A61K 8/418 8/414 |
| 6,086,903 A | | 7/2000 | Trinh et al. | |
| 6,211,139 B1 | * | 4/2001 | Keys | C07C 219/06 510/504 |
| 2011/0146001 A1 | | 6/2011 | Woo et al. | |

FOREIGN PATENT DOCUMENTS

| | | |
|---|---|---|
| JP | H07088168 A | 4/1995 |
| JP | 2001303090 A | 10/2001 |
| JP | 2004143638 A | 5/2004 |
| KR | 20120082952 A | 7/2012 |
| KR | 20150070937 A | 6/2015 |
| WO | WO-2011084463 A1 * | 7/2011 ........... C11D 3/0068 |

OTHER PUBLICATIONS

English Machine Translation for KR20150070937A obtained at https://worldwide.espacenet.com/publicationDetails/biblio?DB=EPODOC&II=1&ND=3&adjacent=true&locale=en_EP&FT=D&date=20150625&CC=KR&NR= (Year: 2015).*
Uniquat 2250 Product Data Sheet by Lonza. Obtained Oct. 27, 2020 at lonza.picturepark.com.*
Search report from International Application No. PCT/KR2016/003207, dated Dec. 26, 2016.

* cited by examiner

*Primary Examiner* — Arrie L Reuther
(74) *Attorney, Agent, or Firm* — Lerner, David, Littenberg, Krumholz & Mentlik, LLP

(57) ABSTRACT

The present disclosure relates to a perfume composition containing an aldehyde perfume ingredient, more particularly to a perfume composition capable of inhibiting odor and unpleasant smell, which may arise when using a formulation containing an amine. The perfume composition of the present disclosure contains a green aldehyde perfume and, thereby, is capable of inhibiting odor and unpleasant smell which arise from a cationic material including an amine. In addition, by mixing a floral or citrus perfume, luxurious and long-lasting fragrance can be provided.

9 Claims, No Drawings

PERFUME COMPOSITION CAPABLE OF MASKING ODOR OF FORMULATION CONTAINING AMINE

CROSS-REFERENCE TO RELATED APPLICATIONS

The present application is a national phase entry under 35 U.S.C. § 371 of International Application No. PCT/KR2016/003207 filed Mar. 29, 2016, the disclosure of which is incorporated herein by reference.

TECHNICAL FIELD

The present disclosure relates to a perfume composition containing an aldehyde perfume ingredient, more particularly to a perfume composition capable of masking odor and unpleasant smell which may arise when using a formulation containing an amine compound.

BACKGROUND ART

In general, daily supplies and cosmetics are used to maintain clean and healthy life. It is common to mix various materials and ingredients in order to provide improved function and effect. But, some ingredients negatively affect usability and emotional desire due to odor and unpleasant smell.

In particular, the amines of cationic surfactants or cationic polymers used in products often cause foul odor, stench, etc. This odor should be improved because even a slight odor is considered as an important defect of the product. Many manufacturers are making efforts to control the odor and unpleasant smell of products because they directly affect the consumers' interest and negatively affect customer satisfaction.

In general, a perfume used to mask the odor of a formulation often has a volatility (b.p.) of 250° C. or lower. Because a perfume having a low volatility evaporates strongly and easily it can instantly mask odor, but the masking effect against the odor felt after the use of a product or during the storage of the product does not last long enough. In addition, as the fragrance characteristics are simple, there are limitations in embodying superior and distinguishable perceived quality.

A common method to reduce the odor and unpleasant smell of a product is to increase the incidence rate. However, if the incidence rate is excessively high, it is problematic in terms of product stability, change in odor with time, and product cost. Another method used to mask odor is to enhance the long-lasting quality. A way to enhance the long-lasting quality is to use a perfume with high contents of ingredients having a boiling point of at least 250° C. and ingredients having a ClogP, which is a measure of solubility, of at least 3 (U.S. Pat. No. 6,086,903). Because the boiling point of a material is inversely proportional to its vapor pressure, a perfume has a scent that lasts longer as the boiling point gets higher. The ClogP is a value obtained by taking logarithm of P, which is the ratio of solubility of a perfume dissolved in octanol and in water. Since a perfume having a higher ClogP value has a lipophilic property, it provides long-lasting scent because the amount of the perfume washed off with water is decreased when it is used in washoff products. However, these perfumes are limited in that scent release is weak during the use of the products and the fragrance is not diverse.

Although various methods are employed to remove the odor or unpleasant smell arising from a formulation containing an amine as described above because the odor greatly affects the quality perceived by consumers, it is very difficult to achieve both the desired fragrance and intensity and satisfy the consumers' sensation.

DISCLOSURE

Technical Problem

The present disclosure is directed to providing a perfume composition capable of masking odor and unpleasant smell such as foul odor, stench, etc. from a product containing a cationic ingredient such as a cationic polymer, a cationic surfactant, etc. containing an amine.

The present disclosure is also directed to providing a personal care composition or a home care composition with odor and unpleasant smell removed, which contains the perfume composition.

Technical Solution

The present disclosure provides a perfume composition for inhibiting odor of an amine, which contains an aldehyde perfume. The aldehyde perfume is a compound having an aldehyde group as a functional group.

The inventors of the present disclosure have researched to solve the problem of odor and unpleasant smell arising from a personal care or home care composition containing an amine compound. In doing so, they have identified that the odor can be masked and the perceived quality of luxurious fragrance can be exerted by containing an aldehyde perfume in the composition together with the amine compound and have completed the present disclosure.

In general, a compound perfume may be used to mask the odor of daily supplies, cosmetic products, etc. The compound perfume may contain one or more aldehyde perfume ingredient. In general, the aldehyde perfume used as an ingredient in the compound perfume may be, for example, 2-[(4-methylphenyl)methylene]-heptanal (mimosa heptanal), 2,6-nonadienal, octanal, nonanal, 8,9,10-undecenal, 2-dodecenal (mandarine aldehyde), 9-undecenal, 10-undecenal, undecanal, adoxal (2,6,10-trimethylundec-9-enal), Ald. C-12 (Lauric), 2-methyldecanal (MNA, Ald. C-12), Ald. C-14, anisic aldehyde, bergamal (3,7-dimethyl-2-methylene-6-octenal), canthoxal (2-methyl-3-(4-methoxyphenyl)propanal), citral, cuminic ald., cyclamen ald., cyclemax (3-(p-cumenyl)propionaldehyde), cymal, decyl aldehyde, florahydral, floral super (4,8-dimethyl-4,9-decadienal), floralozone (3-(o-(and p-)ethylphenyl)-2,2-dimethylpropionaldehyde), floropal, geraldehyde (5,9-dimethyl-4,8-decadienal), helional (alpha-methyl-1,3-benzodioxole-5-propanal), trans-2-hexenal, cis-3-hexenal, hexyl cinnamic aldehyde, hydroxycitronellal, isocyclocitral (2,4,6- and 3,5,6-trimethyl-3-cyclohexene-1-carboxaldehyde), limoxal (β,4-dimethylcyclohex-3-ene-1-propan-1-al), lyral (3- and 4-(4-hydroxy-4-methyl-pentyl)cyclohexene-1-carboxaldehyde), melafleur (5,5-dimethyl-octahydro-2-naphthalenecarboxaldehyde), melozone (octahydro-4,7-methano-1H-indenecarbaldehyde), methyl nonyl acetaldehyde, muguet aldehyde ((3,7-dimethyl-6-octenyl)oxy)acetaldehyde), myrac aldehyde (3-(and 4-)(4-methyl-3-pentyl)cyclohex-3-ene-1-carboxaldehyde), P. T. bucinal, phenyl acetaldehyde, phenoxyacetaldehyde, phenyl acetaldehyde dimethyl acetal, 1-methyl-4-(4-methyl-3-pentenyl)cyclohex-3-ene-1-carboxaldehyde, undecyl aldehyde, undecylenic aldehyde, vertoliff (3,6-dimethylcyclohex-3-ene-1-carboxaldehyde), tert-butyl-α-methyl hydrocinnanic aldehyde, tolyl acetaldehyde (parmanyl), vertral (octahydro-1H-4,7-methanoindene-5-carbaldehyde), boronal (2E)-2-methyl-4-(2,6,6-trimethylcyclohex-1-en-1-yl) but-2-enal), scentenal (octahydro-5-methoxy-4,7-methano-1H-indene-2-carboxaldehyde), trifernal (benzenepropanal), acalea TT (2-[(4-methylphenyl)methylene]-heptanal), acetal CD (phenylacetaldehyde glycerylacetal), bourgeonal (3-(4-tert-butylphenyl)propanal), Cetonal® (2-methyl-4-(2,6,6-trimethyl-2(1)-cyclohexen-1-yl)butanal), Citral Lemarome® ((E/Z)-3,7-dimethyl-2,6-octadienal), Citrathal® TECH (3,7-dimethyl-2,6-octadienal), decenal-4-trans ((E)-4-decenal), decenal-9 (9-decenal)), leguminal (propanal-3-hexenyl methyl acetal), Liffarome™ (cis-3-hexen-1-yl methyl carbonate), mefranal (3-methyl-5-phenylpentanal), melonal (2,6-dimethylhept-5-enal), myraldene (4(3)-(4-methylpent-3-enyl)cyclohex-3-enecarbaldehyde), profarnesal ((5E)-2,6,10-trimethylundeca-5,9-dienal), syringa aldehyde ((4-methylphenyl)acetaldehyde), tetrahydrocitral (3,7-dimethyloctanal), Triplal® (2,4-dimethyl-3-cyclohexene-1-carboxaldehyde), vertocitral (2,4-dimethylcyclohex-3-ene-1-carbaldehyde), vertoliff ISO (3,6- (and 4,6-)dimethylcyclohex-3-ene-1-carboxaldehyde), etc., although not being limited thereto. These perfumes not only exhibit different fragrance characteristics but also have different physical and chemical properties.

In the perfume composition for inhibiting odor of an amine according to the present disclosure, the aldehyde perfume may be a green perfume.

The present disclosure also provides a perfume composition for inhibiting odor of an amine, which further contains a floral perfume.

The present disclosure also provides a perfume composition for inhibiting odor of an amine, which further contains a citrus perfume.

The inventors of the present disclosure have completed the present disclosure by finding an optimum combination of perfume ingredients that effectively mask the odor of an amine They have identified that the green fragrance exhibits the most superior masking effect and a better effect is achieved when the floral fragrance is used in addition to the green fragrance. Also, the citrus fragrance may be further added to provide complete perceived quality of the fragrance.

The green perfume, floral perfume and citrus perfume ingredients are listed in Table 1. However, the perfume ingredients that may be used in the composition of the present disclosure are not limited to those listed in Table 1.

TABLE 1

| Fragrance | Ingredients | Clog P | Chemical name |
|---|---|---|---|
| Green | trans-2-hexenal | 1.79 | (E)-hex-2-enal |
| | cis-3-hexenal | 1.43 | (Z)-hex-3-enal |
| | 2,6-nonadienal | 2.79 | (E,Z)-2,6-nonadien-1-al |
| | Adoxal | >6.0 | 2,6,10-Trimethylundec-9-enal |
| | Aldehyde C9 | 3.27 | Nonanal |
| | Isocyclo citral | 2.87 | (2,4,6-) & (3,5,6-)trimethyl-3-cyclohexene-1-carboxaldehyde |
| | Leguminal | 2.95 | Propanal-3-hexenyl methyl acetal |
| | Liffarome ™ | 2.47 | cis-3-Hexen-l-yl methyl carbonate |
| | Melonal | 3.4 | 2,6-Dimethylhept-5-enal |
| | Melozone | 3.01 | tricyclo[5.2.1.02,6]decane-3-carbaldehyde |
| | Nonadienal | 0.01 | 2,6-Nonadienal |
| | Phenylacetaldehyde | 1.78 | Phenylacetaldehyde |
| | Tolyl acetaldehyde para | 2.09 | p-Tolylacetaldehyde |
| | Triplal ® | 3.1 | 2,4-Dimethyl-3-cyclohexene-1-carboxaldehyde |
| | Vertocitral | 2.34 | 2,4-Dimethylcyclohex-3-ene-1-carbaldehyde |
| | Vertoliff | 3.1 | 3,6-dimethylcyclohex-3-ene-1-carboxaldehyde |
| | Vertoliff ISO | 2.5 | 3,6(and 4,6)-dimethylcyclohex-3-ene-1-carboxaldehyde |
| | Vertral | 2.87 | Octahydro-1H-4,7-methanoindene-5-carbaldehyde |
| Floral | Acalea TT | 5.26 | 2-[(4-methylphenyl)methylene]-heptanal |
| | Acetal CD | 0.8 | Phenylacetaldehyde glycerylacetal |
| | Bergamal | 3.94 | 3,7-Dimethyl-2-methylene-6-octenal |
| | Boronal | 5.24 | (2E)-2-methyl-4-(2,6,6-trimethylcyclo-1-en-1yl)but-2-enal |
| | Bourgeonal | 3.7 | 3-(4-tert-Butylphenyl)propanal |
| | Cetonal ® | 5.5 | 2-Methyl-4-(2,6,6-trimethyl-2(1)-cyclohexen-1-yl)butanal |
| | Cyclamen Aldehyde | 3.43 | 2-Methyl-3-(4-isopropylphenyl)propanal |
| | Cyclemax ™ | 3.37 | 3-(p-cumenyl)propionaldehyde |
| | Floral Super | 4.38 | 4,8-Dimethyl-4,9-decadienal |
| | Floralozone | 3.9 | 3-(o-(and p-)Ethylphenyl)-2,2-dimethylpropionaldehyde |
| | Florhydral ® | 3.8 | 3-(3-Isopropylphenyl)butanal |
| | Helional ™ | 2.4 | alpha-Methyl-1,3-benzodioxole-5-propanal |
| | 10-undecenal | 3.97 | 10-undecenal |
| | Lyral ® | 2.1 | 3-and-(4-Hydroxy-4-methyl-pentyl)cyclohexene-1-carboxaldehyde |
| | Melafleur | 4.38 | 5,5-Dimethyl-octahydro-2-naphthalenecarboxaldehyde |
| | Muguet aldehyde | 3.26 | ((3,7-Dimethyl-6-octenyl)oxy)acetaldehyde |
| | Profarnesal | 5.04 | (5E)-2,6,10-Trimethylundeca-5,9-dienal |
| | Syringa Aldehyde | 4.4 | (4-Methylphenyl)acetaldehyde |
| Citrus | Citral Lemarome ® N | 3.1 | (E/Z)-3,7-Dimethyl-2,6-octadienal |
| | Citronellal | 3.29 | 3,7-dimethyloct-6-enal |
| | Citrathal ® TECH | 3.7 | 3,7-Dimethyl-2,6-octadienal |
| | Decenal-4-Trans | 3-8 | (E)-4-Decenal |
| | Decenal-9 | 3.6 | 9-Decenal |

TABLE 1-continued

| Fragrance | Ingredients | Clog P | Chemical name |
|---|---|---|---|
| | Geraldehyde | 4.43 | 5,9-Dimethyl-4,8-decadienal |
| | Limoxal | 3.84 | ß,4-dimethylcyclohex-3-ene-1-propan-1-al |
| | Mandarine Aldehyde | 5.3 | (E)-2-Dodecenal |
| | Mefranal | 3.3 | 3-Methyl-5-phenylpentanal |
| | Myraldene | 4.4 | 4(3)-(4-Methylpent-3-enyl)cyclohex-3-enecarbaldehyde |
| | Tetrahydro Citral | 3.7 | 3,7-Dimethyloctanal |

The green perfume may be one or more selected from a group consisting of trans-2-hexenal, cis-3-hexenal, 2,6-nonadienal, adoxal (2,6,10-trimethylundec-9-enal), nonanal, isocyclocitral, propanal-3-hexenyl methyl acetal, cis-3-hexen-1-yl methyl carbonate, 2,6-dimethylhept-5-enal, tricyclo[5.2.1.02,6]decane-3-carbaldehyde, 2,6-nonadienal, phenylacetaldehyde, p-tolylacetaldehyde, 2,4-dimethyl-3-cyclohexene-1-carboxaldehyde, 2,4-dimethylcyclohex-3-ene-1-carbaldehyde, 3,6-dimethylcyclohex-3-ene-1-carboxaldehyde, 3,6- (and 4,6-)dimethylcyclohex-3-ene-1-carboxaldehyde and octahydro-1H-4,7-methanoindene-5-carbaldehyde, although not being limited thereto. Specifically, two or more green perfumes may be used to embody luxurious fragrance when using the composition of the present disclosure.

The floral perfume is used to more effectively mask the order of an amine and may be one or more selected from a group consisting of 2-[(4-methylphenyl)methylene]-heptanal, phenylacetaldehyde, phenylacetaldehyde glycerylacetal, bergamal, boronal, bourgeonal, 2-methyl-4-(2,6,6-trimethyl-2(1)-cyclohexen-1-yl)butanal, cyclamen aldehyde, 3-(p-cumenyl)propionaldehyde, 4,8-dimethyl-4,9-decadienal, 3-(o-(and p-)ethylphenyl)-2,2-dimethylpropionaldehyde, 3-(3-isopropylphenyl)butanal, helional, 10-undecenal, lyral, melafleur, muguet aldehyde, profarnesal and syringa aldehyde ((4-methylphenyl)acetaldehyde), although not being limited thereto.

The citrus perfume is used to improve the perceived quality of the fragrance and may be one or more selected from a group consisting of (E/Z)-3,7-dimethyl-2,6-octadienal, citronellal, 3,7-dimethyl-2,6-octadienal, decenal-4-trans, decenal-9, geraldehyde, limoxal, mandarine aldehyde, mefranal, myraldene and tetrahydrocitral, although not being limited thereto.

The present disclosure also provides a perfume composition which contains a perfume with a ClogP of 4 or lower in an amount of at least 30 wt % based on the total weight of the composition. The ClogP is a value obtained by taking logarithm of P, which is the ratio of solubility of a perfume dissolved in octanol and in water. To achieve more superior effect of masking the odor of an amine, the amount of the perfume with a ClogP of 4 or lower may be more specifically at least 50 wt %, most specifically at least 70 wt %, based on the total weight of the composition.

The aldehyde perfume may be contained in an amount of 5-50 wt % based on the total weight of the perfume. If the amount of the aldehyde perfume is less than 5 wt % based on the total weight of the perfume, the odor-masking effect is insignificant. And, if it exceeds 50 wt %, the preference for the perfume is decreased.

The present disclosure provides a personal care composition or a home care composition containing the aldehyde perfume composition. The personal care composition may be a skin care composition such as a skin lotion, an essence, a lotion, an eye cream, a cream, etc., a hair care composition such as a hair dye, a shampoo, a conditioner, a treatment, a hair essence, etc. or a body care composition such as a body cleanser, a body lotion, a soap, etc. However, it may be any personal care composition to which a perfume is added, without being limited thereto. The home care composition may be a fabric care composition such as a detergent, a fabric softener, etc., a dish detergent, an aromatic, etc. However, it may be any home care composition to which a perfume is added, without being limited thereto.

The home care product or the personal care product may commonly contain a cationic ingredient such as a cationic polymer or a cationic surfactant, an amphoteric surfactant, a nonionic surfactant, a nonionic polymer, etc., the kind and addition amount of which are different depending on the desired purpose and function. The cationic ingredient plays an important role in maintaining the long-lasting scent of the fragrance after use of the product. In general, the products for maintaining long-lasting scent after washoff include hair care products such as a shampoo, a hair conditioner or a hair dye, fabric care products such as a detergent or a fabric softener, etc. A hair dye for dyeing hair requires the maintenance of long-lasting scent because the dye ingredient has offensive odor.

The present disclosure provides a hair care composition containing the perfume composition and one or more selected from a group consisting of a cationic surfactant, an amphoteric surfactant, a nonionic surfactant and a cationic polymer.

The cationic surfactant used in the hair care composition may be one or more selected from a group consisting of cetrimonium chloride, stearamidopropyl dimethylamine, dicetyl dimethyl ammonium chloride and ester quatro, although not being limited thereto.

The amphoteric surfactant used in the hair care composition may be one or more selected from a group consisting of cocamidopropyl betaine, cocoamphocarboxyglycinate and cocoamphocarboxypropionate, although not being limited thereto.

The nonionic surfactant used in the hair care composition may be one or more selected from a group consisting of lauric diethanolamide, coconut diethanolamide, coconut monoethanolamide, lauryldimethylamine oxide and coconut alkyldimethylamine oxide, although not being limited thereto.

The cationic polymer used in the hair care composition may be one or more selected from a natural cationic polymer group consisting of guar hydroxypropyltrimonium chloride, hydroxypropyl guar hydroxypropyltrimonium chloride and quaternary hydroxyethyl cellulose and a synthetic cationic polymer consisting of a dimethyldiallylammonium chloride polymer, an acrylamide dimethyldiallylammonium chloride copolymer and a polyvinylpyrrolidone dimethylaminoethyl methacrylate copolymer, although not being limited thereto.

The present disclosure also provides a fabric care composition containing the perfume composition and a cationic polymer, an amphoteric surfactant or a mixture thereof.

The cationic polymer used in the fabric care composition may be one or more selected from a group consisting of cationic guar, cationic cellulose, a dimethyldiallylammonium chloride polymer, an acrylamide-dimethyldiallylammonium chloride copolymer, a PVP-dimethylaminoethyl methacrylate copolymer, an acrylic acid-dimethyldiallylammonium chloride copolymer, an acrylamide-dimethylaminoethyl methacrylate methyl chloride copolymer and a trimethylaminoethyl methacrylate polymer, although not being limited thereto.

The amphoteric surfactant used in the fabric care composition may be one or more selected from a group consisting of alkyl amidopropyl betaine, alkyl dimethyl betaine, alkyl monoamphoacetate, cocoamphocarboxyglycinate, sarcosinate and alkyl amphodiacetate, although not being limited thereto.

The present disclosure also provides a hair dye composition containing the perfume composition, a precursor and a coupler.

The precursor used in the hair dye composition may be one or more selected from a group consisting of 2-chloro-p-phenylenediamine, N-methoxyethyl-p-phenylenediamine, N,N-bis(2-hydroxyethyl)-p-phenylenediamine, 2-(2-hydroxyethyl)-p-phenylenediamine, 2,6-dimethyl-p-phenylenediamine, 4,4'-diaminodiphenylamine, 1,3-bis(N-(2-hydroxyethyl)-N-(4-aminophenyl)amino)-2-propanol, PEG-3,3,2'-p-phenylenediamine, p-aminophenol, p-methylaminophenol, 3-methyl-4-aminophenol, 2-aminomethyl-4-aminophenol, 2-(2-hydroxyethylaminomethyl)-4-aminophenol, o-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, 4,5-diamino-1-hydroxyethylpyrazole and salts thereof, o-aminophenol, p-aminophenol, toluene-2,5-diamine hydrochloride, p-phenylenediamine hydrochloride, toluene-2,5-diamine, p-phenylenediamine, p-methylaminophenol sulfate, o-aminophenol sulfate, p-aminophenol sulfate, toluene-2,5-diamine sulfate and p-phenylenediamine sulfate, although not being limited thereto.

The coupler used in the hair dye composition may be one or more selected from a group consisting of m-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, m-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine and salts thereof, although not being limited thereto.

Advantageous Effects

The perfume composition of the present disclosure, which contains a green aldehyde perfume, can inhibit odor and unpleasant smell caused by a cationic material including an amine. In addition, it can provide luxurious fragrance and long-lasting scent by further containing a floral or citrus perfume.

MODE FOR DISCLOSURE

Hereinafter, the present disclosure is described in detail through examples. However, the examples according to the present disclosure can be modified into various other forms and the scope of the present disclosure should not be interpreted to be limited to the following examples. The examples of the present disclosure are provided to more completely explain the present disclosure to those of ordinary skill in the art.

In the following examples, a hair dye was used to demonstrate the effect of the perfume composition of the present disclosure because the odor caused by an amine is strong and evaluation can be conducted relatively immediately. However, it should not be construed that the scope of the present disclosure is restricted to the hair dye.

EXAMPLE 1

Perfume bases 1 to 3 containing aldehyde perfumes were prepared according to the compositions given in Table 2.

TABLE 2

| | Perfume name | Perfume base 1 | Perfume base 2 | Perfume base 3 |
|---|---|---|---|---|
| Green | Adoxal | 10.0 | 10.0 | 10.0 |
| | trans-2-Hexenal | 2.0 | 2.0 | 2.0 |
| | cis-3-Hexenal | 1.0 | 1.0 | 1.0 |
| | 2,6-Nonadienal | 2.0 | 2.0 | 2.0 |
| | Leguminal | 15.0 | 10.0 | 10.0 |
| | Triplal ® | 12.0 | 10.0 | 10.0 |
| | Vertral | 8.0 | 5.0 | 5.0 |
| Floral | Hydroxycitronellal | — | 3.0 | 5.0 |
| | Cyclamen ald. | — | 3.0 | 5.0 |
| | Helional | — | 5.0 | 5.0 |
| | Lyral | — | 3.0 | 5.0 |
| | Melafleur | — | 5.0 | 5.0 |
| | Hexyl cinnamic aldehyde | — | 1.0 | 2.0 |
| | Jasmal | — | 3.0 | 5.0 |
| | Muguet aldehyde | — | 5.0 | 5.0 |
| | Vertral | — | 2.0 | 3.0 |
| Citrus | Citronellal | — | — | 2.0 |
| | Citral | — | — | 2.0 |
| | Mandarine aldehyde | — | — | 6.0 |
| Solvent | DPG | 50.0 | 20.0 | 10.0 |
| Total | | 100.0 | 100.0 | 100.0 |

Perfume compositions of Preparation Example 1-9 were prepared by mixing the three perfume bases listed in Table 2 with a general-use perfume according to the weight ratios described in Table 3. As the general-use perfume, the Angel berry perfume acquired from Givaudan was used. The Angel berry perfume is a mixture of linalool (dimethyl-1,6-octadien-3-ol), 1,3,4,6,7,8-hexahydro-4,6,6,7,8,8-hexamethylindeno[5,6-c]pyran, benzyl 2-hydroxybenzoate, 2-tert-butylcyclohexyl acetate, cyclopentaneacetic acid, 3-oxo-2-pentyl methyl ester, geraniol ((2E)-3,7-dimethyl-2,6-octadien-1-ol), 4-(2,6,6-trimethylcyclohex-1-en-1-yl)but-3-en-2-one, 3-methyl-4-(2,6,6-trimethyl-2-cyclohexen-1-yl)-3-buten-2-one, 2-phenoxyethyl 2-methylpropanoate, hexyl acetate and 6-acetyl-1,1,2,4,4,7-hexamethyl-1,2,3,4-tetrahydronaphthalene.

TABLE 3

| (wt %) | Prep. Ex. 1 | Prep. Ex. 2 | Prep. Ex. 3 | Prep. Ex. 4 | Prep. Ex. 5 | Prep. Ex. 6 | Prep. Ex. 7 | Prep. Ex. 8 | Prep. Ex. 9 |
|---|---|---|---|---|---|---|---|---|---|
| General-use perfume | 95.0 | 95.0 | 95.0 | 80.0 | 80.0 | 80.0 | 50.0 | 65.0 | 60.0 |
| Perfume base 1 | 5.0 | | | 20.0 | | | 50.0 | | |
| Perfume base 2 | | 5.0 | | | 20.0 | | | 50.0 | |
| Perfume base 3 | | | 5.0 | | | 20.0 | | | 50.0 |
| Total | 100.0 | 100.0 | 100.0 | 100.0 | 100.0 | 100.0 | 100.0 | 100.0 | 100.0 |

The perfume compositions of Preparation Examples 1-9 described in Table 3 were added to an agent 1 described in Table 4 in an amount of 0.7 wt % to prepare nine agent 1 compositions (Examples 1-9). As comparative examples, an agent 1 composition containing no perfume (Comparative Example 1) and an agent 1 composition containing the existing perfume (Comparative Example 2) were prepared. For Comparative Example 1, dipropylene glycol (DPG) which is commonly used as a solvent of a perfume was used instead of the perfume. For Comparative Example 2, a perfume commonly used in a hair dye was used.

TABLE 4

| | No. | Ingredients | Contents (%) |
|---|---|---|---|
| Agent 1 | 1 | Toluene-2,5-diamine | 0.50 |
| | 2 | Resorcinol | 0.40 |
| | 3 | m-Aminephenol | 0.10 |
| | 4 | Sodium cocoyl glutaminate | 7.20 |
| | 5 | Alkyl (8-16) glycoside | 2.00 |
| | 6 | Polyoxyethylene lauryl ether | 2.00 |
| | 7 | Polyoxyethylene tridecyl ether | 0.50 |
| | 8 | Propylene glycol | 4.00 |
| | 9 | Ethanol | 9.50 |
| | 10 | Ammonia | 1.68 |
| | 11 | Ammonium bicarbonate | 8.00 |
| | 12 | Monoethanolamine | 2.40 |
| | 13 | Ascorbic acid | Adequate |
| | 14 | Anhydrous sodium sulfite | Adequate |
| | 15 | Tetrasodium EDTA dehydrate | Adequate |
| | 16 | Perfume | 0.70 |
| | 17 | Purified water | To 100.0 |
| Agent 2 | 1 | Stearyltrimethylammonium chloride | 0.70 |
| | 2 | Polyoxyethylene (40) cetyl ether | 0.46 |
| | 3 | Cetanol | 0.74 |
| | 4 | Myristyl alcohol | 0.21 |
| | 5 | Hydroxyethane diphosphonate | 0.04 |
| | 6 | Oxyquinoline sulfate | 0.01 |
| | 7 | Sodium hydroxide | Adequate |
| | 8 | Hydrogen peroxide | 5.70 |
| | 9 | Purified water | To 100.0 |

Test Example: Sensory Evaluation of Amine Odor

After mixing 50 g of the agent 1 and 30 g of the agent 2 described in Table 4, hair dyeing was conducted by applying the mixture on a hair tress. The odor of amine was evaluated immediately after the dyeing, 20 minutes after the dyeing and after washoff.

The sensory evaluation was conducted by 15 people aged in their 20s to 40s with experiences in hair dyeing. Their average age was 31.5 years (5 men and 10 women). The criteria of the sensory evaluation was as follows.

—Criteria of Sensory Evaluation—

Score 1: Very intense amine odor (similar to squid smell).
Score 2: Intense amine odor.
Score 3: Moderate amine odor.
Score 4: Weak amine odor.
Score 5: Very weak amine odor.

The result of sensory evaluation immediately after the dyeing is shown in Table 5. The result of sensory evaluation 20 minutes after the dyeing is shown in Table 6. And, the result of sensory evaluation after the washoff is shown in Table 7.

TABLE 5

| | Comp. Ex. 1 | Comp. Ex. 2 | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Mean | 1.32 | 1.98 | 2.45 | 2.54 | 2.54 | 2.93 | 3.01 | 3.02 | 3.27 | 3.29 | 3.20 |
| SD | 0.62 | 0.62 | 0.56 | 0.64 | 0.70 | 0.80 | 0.70 | 0.72 | 0.80 | 0.59 | 0.86 |

TABLE 6

| | Comp. Ex. 1 | Comp. Ex. 2 | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Mean | 1.47 | 2.13 | 2.80 | 2.93 | 2.93 | 3.37 | 3.45 | 3.43 | 3.60 | 3.61 | 3.53 |
| SD | 0.64 | 0.64 | 0.68 | 0.59 | 0.70 | 0.70 | 0.70 | 0.72 | 0.83 | 0.74 | 0.83 |

TABLE 7

| | Comp. Ex. 1 | Comp. Ex. 2 | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Mean | 2.87 | 3.00 | 3.40 | 3.48 | 3.48 | 4.08 | 4.10 | 4.10 | 4.08 | 4.44 | 4.42 |
| SD | 0.64 | 0.65 | 0.63 | 0.62 | 0.62 | 0.74 | 0.63 | 0.70 | 0.64 | 0.70 | 0.72 |

Referring to the result of Table 5, there was a significant difference in amine odor between Comparative Example 1 not treated with a perfume and Comparative Example 2 treated with the existing perfume immediately after the dyeing. In addition the amine odor-masking effect was improved as the content of the aldehyde perfume was increased.

Referring to the result of Table 5 and Table 6, when comparing the results for Comparative Example 1 and Comparative Example 2 immediately after the dyeing and 20 minutes after the dyeing, the amine odor was stronger 20 minutes after the dyeing than immediately after the application of the hair dye. However, for Examples 1-9 wherein the aldehyde perfume was contained, the amine odor was comparable or slightly weaker 20 minutes after the dyeing.

Referring to the result of Table 7, the amine odor-masking effect was superior for Comparative Example 2 wherein the general-use perfume was contained as compared to Comparative Example 1 wherein no perfume was contained after washing off the hair dye, suggesting that a perfume has an odor-masking effect.

In addition, the odor-masking effect was more superior for Examples 1-9 wherein the aldehyde perfume composition was contained as compared to Comparative Example 2. The correlation coefficient was calculated to be 0.976, which suggests that the amine odor-masking effect is more superior as the content of the aldehyde perfume is higher.

What is claimed is:

1. A method for inhibiting odor of a personal care or household care composition comprising at least one cationic ingredient selected from the group consisting of a cationic surfactant, an amphoteric surfactant and a cationic polymer,
    wherein the cationic surfactant is selected from cetrimonium chloride, or stearamidopropyl dimethylamine, the amphoteric surfactant is selected from cocamidopropyl betaine, cocoamphocarboxyglycinate cocoamphocarboxypropionate, alkyl amidopropyl betaine, alkyl dimethyl betaine, alkyl monoamphoacetate, sarcosinate, or alkyl amphodiacetate, and the cationic polymer is selected from cationic guar, cationic cellulose, a dimethyldiallylammonium chloride polymer, an acrylamide dimethyldiallylammonium chloride copolymer, a polyvinylpyrrolidone dimethylaminoethyl methacrylate copolymer, an acrylic acid-dimethyldiallylammonium chloride copolymer, an acrylamide-dimethylaminoethyl methacrylate methyl chloride copolymer, or a trimethylaminoethyl methacrylate polymer,
    wherein the odor results from the at least one cationic ingredient, and
    wherein the method comprises adding a compound having an aldehyde group to the personal care or household care composition.

2. The method according to claim 1, wherein the compound having an aldehyde group is one or more selected from the group consisting of trans-2-hexenal, cis-3-hexenal, 2,6-nonadienal, adoxal (2,6,10-trimethylundec-9-enal), nonanal, isocyclocitral, propanal-3-hexenyl methyl acetal, cis-3-hexen-1-yl methyl carbonate, 2,6-dimethylhept-5-enal, tricyclo[5.2.1.02,6]decane-3-carbaldehyde, phenylacetaldehyde, p-tolylacetaldehyde, 2,4-dimethyl-3-cyclohexene-1-carboxaldehyde, 2,4-dimethylcyclohex-3-ene-1-carbaldehyde, 3,6-dimethylcyclohex-3-ene-1-carboxaldehyde, 3,6- (and 4,6-)dimethylcyclohex-3-ene-1-carboxaldehyde and octahydro-1H-4,7-methanoindene-5-carbaldehyde.

3. The method according to claim 2, wherein the method further comprises adding one or more ingredients selected from the group consisting of 2-[(4-methylphenyl)methylene]-heptanal, phenylacetaldehyde, phenylacetaldehyde glycerylacetal, bergamal, boronal, bourgeonal, 2-methyl-4-(2,6,6-trimethyl-2(1)-cyclohexen-1-yl)butanal, cyclamen aldehyde, 3-(p-cumenyl)propionaldehyde, 4,8-dimethyl-4,9-decadienal, 3-(o-(and p-)ethylphenyl)-2,2-dimethylpropionaldehyde, 3-(3-isopropylphenyl)butanal, helional, 10-undecenal, lyral, melafleur, muguet aldehyde, profarnesal and syringa aldehyde ((4-methylphenyl)acetaldehyde) to the personal care or household care composition.

4. The method according to claim 3, wherein the method further comprises adding one or more ingredients selected from the group consisting of (E/Z)-3,7-dimethyl-2,6-octadienal, citronellal, 3,7-dimethyl-2,6-octadienal, decenal-4-trans, decenal-9, geraldehyde, limoxal, mandarine aldehyde, mefranal, myraldene, and tetrahydrocitral to the personal care or household care composition.

5. The method according to claim 1, wherein the compound having an aldehyde is added in an amount of 5-50 wt % based on the total weight of the personal care or household care composition.

6. The method according to claim 1, wherein the personal care or household care composition comprises a perfume with a ClogP of 4 or lower in an amount of at least 30 wt % based on the total weight of the personal care or household care composition.

7. A method for inhibiting odor of a hair care composition comprising at least one cationic ingredient selected from the group consisting of a cationic surfactant and a cationic polymer,
    wherein the cationic surfactant is selected from cetrimonium chloride, or stearamidopropyl dimethylamine, and the cationic polymer is selected from guar hydroxypropyltrimonium chloride, hydroxypropyl guar hydroxypropyltrimonium chloride, quaternary hydroxyethyl cellulose, a dimethyldiallylammonium chloride polymer, an acrylamide dimethyldiallylammonium chloride copolymer, or a polyvinylpyrrolidone dimethylaminoethyl methacrylate copolymer,
    wherein the odor results from the at least one cationic ingredient, and
    wherein the method comprises adding a compound having an aldehyde group to the hair care composition.

8. The method according to claim 7, wherein the hair care composition is a hair dye composition,
    wherein the cationic ingredient comprises a precursor and a coupler,
    wherein the precursor is one or more selected from the group consisting of 2-chloro-p-phenylenediamine, N-methoxyethyl-p-phenylenediamine, N,N-bis(2-hydroxyethyl)-p-phenylenediamine, 2-(2-hydroxyethyl)-p-phenylenediamine, 2,6-dimethyl-p-phenylenediamine, 4,4'-diaminodiphenylamine, 1,3-bis(N-(2-hydroxyethyl)-N-(4-aminophenyl)amino)-2-propanol, PEG-3,3,2'-p-phenylenediamine, p-aminophenol, p-methylaminophenol, 3-methyl-4-aminophenol, 2-aminomethyl-4-aminophenol, 2-(2-hydroxyethylaminomethyl)-4-aminophenol, o-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, 4,5-diamino-1-hydroxyethylpyrazole and salts thereof, o-aminophenol, p-aminophenol, toluene-2,5-diamine hydrochloride, p-phenylenediamine hydrochloride, toluene-2,5-diamine, p-phenylenediamine, p-methylaminophenol sulfate, o-aminophenol sulfate, p-aminophenol sulfate, toluene-2,5-diamine sulfate, and p-phenylenediamine sulfate; and the coupler is one or more selected from the group consisting of m-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, m-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine, and salts thereof.

9. A method for inhibiting odor of a fabric care composition comprising at least one cationic ingredient comprising a cationic polymer, wherein the cationic polymer is selected from cationic guar, cationic cellulose, a dimethyldiallylammonium chloride polymer, an acrylamide-dimethyldiallylammonium chloride copolymer, a PVP-dimethylaminoethyl methacrylate copolymer, an acrylic acid-dimethyldiallylammonium chloride copolymer, an acrylamide-dimethylaminoethyl methacrylate methyl chloride copolymer or a trimethylaminoethyl methacrylate polymer, wherein the odor results from the at least one cationic ingredient-, and wherein the method comprises adding a compound having an aldehyde group to the fabric care composition.

* * * * *